(12) United States Patent
Maltbie et al.

(10) Patent No.: US 8,737,704 B2
(45) Date of Patent: May 27, 2014

(54) METHODS FOR ANALYZING ABSORBENT ARTICLES

(75) Inventors: David John Maltbie, Hamilton, OH (US); Thomas Edward Dufresne, Morrow, OH (US); Joseph Henry Nurre, West Chester, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 379 days.

(21) Appl. No.: 13/161,733

(22) Filed: Jun. 16, 2011

(65) Prior Publication Data

US 2011/0243425 A1 Oct. 6, 2011

Related U.S. Application Data

(63) Continuation-in-part of application No. 12/586,089, filed on Sep. 17, 2009, which is a continuation-in-part of application No. 11/890,835, filed on Aug. 8, 2007, now Pat. No. 7,949,163.

(60) Provisional application No. 60/836,299, filed on Aug. 8, 2006.

(51) Int. Cl.
*G06K 9/00* (2006.01)

(52) U.S. Cl.
USPC .......................... 382/128; 382/131; 382/132

(58) Field of Classification Search
CPC ............................................... A61F 13/15203
USPC ................................ 382/128, 130, 131, 132
See application file for complete search history.

(56) References Cited

U.S. PATENT DOCUMENTS

| 5,171,302 | A | 12/1992 | Buell |
| 5,419,729 | A | 5/1995 | Gross |
| 6,217,890 | B1 * | 4/2001 | Paul et al. ..................... 424/402 |
| 6,659,992 | B1 | 12/2003 | Schmidt et al. |

(Continued)

FOREIGN PATENT DOCUMENTS

| EP | 1595465 B1 | 11/2005 |
| EP | 2224362 A1 | 9/2010 |

(Continued)

OTHER PUBLICATIONS

Siegfried Stapf, Song-I Han, Hardware and Materials, NMR Imaging in Chemical Engineering, 2006, pp. 47-76, Wiley-VCH Verlag GmbH & Co. KGaA, Weinheim.

(Continued)

*Primary Examiner* — Tom Y Lu
(74) *Attorney, Agent, or Firm* — Andres E. Velarde; Andrew A. Paul (57) ABSTRACT

A method for analyzing an absorbent article may include providing a three-dimensional computed tomography data set comprising a mannequin image and an article image. The article image may be constructed from projections collected while the absorbent article is fitted to a mannequin. An outer surface of the mannequin image may be identified. A desired distance may be provided. A volumetric demarcation may be spaced the desired distance away from the outer surface of the mannequin image. An image volume may be disposed between the outer surface of the mannequin image and the volumetric demarcation. A relevant portion of the article image may be enhanced using a processor. The relevant portion of the article image may be coincident with the image volume.

25 Claims, 6 Drawing Sheets

(56) References Cited

U.S. PATENT DOCUMENTS

| | | |
|---|---|---|
| 6,766,817 B2 | 7/2004 | da Silva |
| 6,839,402 B2 | 1/2005 | Stabe et al. |
| 6,904,820 B2 | 6/2005 | Tate et al. |
| 6,918,404 B2 | 7/2005 | da Silva |
| 6,931,951 B2 | 8/2005 | Wright et al. |
| 7,066,586 B2 | 6/2006 | da Silva |
| 7,174,774 B2 | 2/2007 | Pawar et al. |
| 7,459,866 B2 | 12/2008 | Yu et al. |
| 7,549,866 B2 * | 6/2009 | Cohen et al. .................. 434/267 |
| 7,663,648 B1 | 2/2010 | Saldanha et al. |
| 7,712,640 B2 | 5/2010 | Honer et al. |
| 7,949,163 B2 * | 5/2011 | Honkonen et al. ............ 382/128 |
| 2007/0048709 A1 | 3/2007 | Ales, III et al. |
| 2008/0004833 A1 | 1/2008 | Becker |
| 2008/0034849 A1 | 2/2008 | Honkonen et al. |
| 2008/0049899 A1 | 2/2008 | Rothschild |
| 2008/0253525 A1 | 10/2008 | Boyden et al. |
| 2010/0116036 A1 | 5/2010 | Honkonen et al. |

FOREIGN PATENT DOCUMENTS

| | | |
|---|---|---|
| JP | 2003-067725 A | 3/2003 |
| WO | WO 96/12459 A2 | 5/1996 |
| WO | WO 2005/088484 A1 | 9/2005 |
| WO | WO 2007/146152 A2 | 12/2007 |
| WO | WO 2009/026492 | 2/2009 |

OTHER PUBLICATIONS

Siegfried Stapf, Song-I Han, Fluids and Flows, NMR Imaging in Chemical Engineering, 2006, pp. 359-382, Wiley-VCH Verlag GmbH & Co. KGaA, Weinheim.

Siegfried Stapf, Song-I Han, NMR For Food Quality Control, NMR Imaging in Chemical Engineering, 2006, pp. 471-489, Wiley-VCH Verlag GmbH & Co. KGaA, Weinheim.

International Search Report, PCT/US2007/017703, mailed Mar. 19, 2008, 11 pages.

T.J. Heindel et al., "An X-ray system for visualizing fluid flows", Flow Measurement and Instrumentation 19 (2008), pp. 67-78.

J.M. Wells, "On Non-Destructive Evaluation Techniques For Ballistic Impact Damage In Armor Ceramics", pp. 238-248.

* cited by examiner

METHODS FOR ANALYZING ABSORBENT ARTICLES

CROSS-REFERENCE TO RELATED APPLICATIONS

This application is a continuation-in-part of prior U.S. application Ser. No. 12/586,089, filed on Sep. 17, 2009, which is a continuation-in-part of prior U.S. application Ser. No. 11/890,835, filed on Aug. 8, 2007 now U.S. Pat. No. 7,949,163, which claims the benefit of U.S. Provisional Application No. 60/836,299, filed on Aug. 8, 2006, all of which are incorporated herein by reference.

FIELD OF THE INVENTION

The present specification generally relates to methods for analyzing absorbent articles and, more specifically, methods for analyzing absorbent articles using three-dimensional computed tomography.

BACKGROUND OF THE INVENTION

Observing and/or analyzing the interior of various consumer products can provide useful or important information to the product's manufacturer or others. For example, the manufacturer may want to observe the interior of the product and its constituents or components at any of several stages, including during product design, during manufacture, after the manufacture but before the product is packaged, when the product is in its packaging, upon opening of the package, upon removal of the product from the packaging, when the product is in actual or simulated use conditions, etc. Given that products and components thereof may exhibit different characteristics in a wet state versus a dry state, it may be desirable to have a method available which can allow observation and/or analysis of the same product in a dry state, then after the introduction of liquid, in a wet state, and after the introduction of additional liquid, a yet wetter state, and so on. Further, an illustrative but nonexclusive list of entities that may find it desirable to observe the interiors of products and their packaging includes, but is not limited to, manufacturers, competitors, distributors, consumers or consumer groups, quality control organizations, certification organizations, governmental agencies, and so on. A manufacturer also may desire to observe the interior of many other products and their packaging. For example, a manufacturer may want to observe the interior of various liquids, semi-solids, emulsions, and colloids, such as in their packaging. A manufacturer also may desire to observe the interior of any of a variety of products and packaging such as, for example, absorbent articles. Accordingly, a need exists for alternative methods for analyzing absorbent articles.

SUMMARY OF THE INVENTION

In one example, a method for analyzing an absorbent article may include providing a three-dimensional computed tomography data set comprising a mannequin image and an article image. The article image may be constructed from projections collected while the absorbent article is fitted to a mannequin. An outer surface of the mannequin image may be identified. A desired distance may be provided. A volumetric demarcation may be spaced the desired distance away from the outer surface of the mannequin image. An image volume may be disposed between the outer surface of the mannequin image and the volumetric demarcation. A relevant portion of the article image may be enhanced using a processor. The relevant portion of the article image may be coincident with the image volume.

In another example, a method for analyzing an absorbent article may include providing a three-dimensional computed tomography data set comprising a mannequin image and an article image. The article image may be constructed from projections collected while the absorbent article is fitted to a mannequin. An outer surface of the mannequin image and a spatial location of the article image may be identified. A shortest distance from the spatial location of the article image to the outer surface of the mannequin image may be calculated using a processor. A predicted performance characteristic may be generated. The predicted performance characteristic may be based at least in part upon the shortest distance.

In yet another example, a method for analyzing an absorbent article may include providing a predicted performance characteristic of the absorbent article. A first three-dimensional computed tomography data set comprising a first article image may be provided using a processor. A second three-dimensional computed tomography data set comprising a second article image may be provided. The first article image and the second article image may be compared to the predicted performance characteristic. The first three-dimensional computed tomography data set and the second three-dimensional computed tomography data set may be constructed from projections collected while the absorbent article is fitted to a mannequin. The first article image may be indicative of the absorbent article throughout a first time period. The second article image may be indicative of the absorbent article throughout a second time period.

These and additional features provided by the examples described herein will be more fully understood in view of the following detailed description, in conjunction with the drawings.

BRIEF DESCRIPTION OF THE DRAWINGS

The drawings are illustrative in nature and not intended to limit the subject matter defined by the claims. The following detailed description can be understood when read in conjunction with the following drawings, where like structure is indicated with like reference numerals and in which:

DETAILED DESCRIPTION OF THE INVENTION

Using the scanning and imaging methods of the present disclosure, it may be desirable for a manufacturer or another to observe and/or analyze the interior of any of a wide range of consumer products. For example, it may be desirable to observe the interior of any product of interest, such as absorbent articles, cleaning products, batteries, beauty care products, medical products, medical devices, food products, and many other products. Absorbent articles for which a manufacturer may want to observe the interior include, for example, bath tissue, paper towels, wipes (e.g., disinfectant, cleansing, facial, hand, baby, perineal), diapers, training pants, catamenial products, wound care dressings, incontinence pads, and bandages. Absorbent articles suitable for use herein are preferably disposable absorbent articles. Cleaning products may include absorbent articles and may further include laundry products such as fabric softener sheets and dish care products such as cleaning foam. Beauty care products may include, for example, antiperspirants, toothpaste, skin care products such as lotion, cosmetics such as pressed powders, and hair care products such as hairspray. Medical products and medical devices may include medications, pharmaceuticals, bandages such as athletic bandages or wound care bandages, syrups, salves, etc. Food products may include, for example, snacks such as chips and crisps, liquids such as oils, emulsions such as margarine, beverages, etc. The examples described herein may be used with any suitable consumer product, any portion or constituent of a consumer product, any of the above in packaging, etc.

Observation of the interior of the products and their packaging as disclosed herein can provide a range of useful information, and it can do so in different contexts. For example, it may be desirable for various products to have a range of performance characteristics. Performance characteristics that may be relevant to certain products may include, by way of example only, the dimensions of the product, whether the product leaks and if so, where and how much, shelf life of the product, fit of the product in-use including determining the area(s) and amount of less than desirable fit, expansion of the product when stored or in-use, contraction of the product when stored or in use, package integrity, how the product is distributed in a package, how the product's constituents are distributed in the product or in the package, how the product reacts in a static state, how the product reacts in a dynamic state, how the product reacts while being used, and many other factors that affect the product, its packaging, etc. An examination of the interior of the product or its packaging may provide information regarding one or more of these characteristics.

Moreover, when a product is made, the product may be made pursuant to various quality or control specifications. Examination of the product's interior, or the interior as it relates to the packaging, may be useful for evaluating compliance with such specifications. In some situations, evaluating compliance with specifications may involve intrusive or destructive examination of the product, which may not provide representative or accurate information regarding the product's characteristics. In other situations, evaluating compliance with specifications may involve intrusive or destructive examination of the product's packaging, which again may not provide representative or accurate information regarding the characteristics of the product or its packaging.

Before a manufacturer begins commercial production of a product, the manufacturer may conduct various testing on the product and its packaging. Before manufacturing a product, the products may be designed and tested using a virtual model, an actual physical product, other suitable methods, or combinations of the above. Virtual models are based on assumptions and calculations. They may predict a product's performance characteristics given a set of circumstances, constraints, boundary conditions and/or environments. Virtual models can be useful to validate and/or supplement actual physical tests or may supplant actual physical testing when, for example, actual physical tests are difficult to perform, if it is hard to generate accurate data, if the tests are generally expensive to conduct, if the tests are to be conducted in vivo, or if the test require the use of personally identifiable information which may pose privacy concerns. Virtual models, however, have their limitations too, and can yield information that differs from how the product and its packaging actually perform or react in various environments.

Moreover, it may be desirable to observe the interior of various products in actual or simulated usage conditions. For purposes of illustration only, one example of a product category whose interior may be of interest during use conditions is absorbent articles. It also may be desirable to observe the interior of many other products and their packaging during use and other conditions. Illustrative absorbent articles include, but are not limited to, diapers, incontinence pads, training pants, tampons, catamenial napkins, paper towels, etc. Each of these examples may include an absorbent core that may receive and hold bodily exudates and/or a sealing member that mitigates the flow of exudates between the absorbent article and a wearer of the absorbent article. Any absorbent article with any suitable absorbent core and/or sealing member may be evaluated according to the methods described herein.

One performance characteristic of absorbent articles that may be of interest is the product's ability to absorb and contain bodily discharges, including initial, subsequent, and continuous or repeated discharges, and the product's ability to contain such discharges without leaking. Another characteristic of absorbent articles that may be of interest to a manufacturer is the actual, as opposed to predicted, flow pattern of liquids as they move through the absorbent article after contacting the absorbent article. The flow path of liquids within the interior of the absorbent article may provide useful information, including but not limited to where the absorbent core should have increased absorptive capacity, how to channel liquids away from areas that may be more susceptible to leakage, how to wick and otherwise control fluid flow, etc. Where a given region of an article is more susceptible to leakage, information regarding the actual flow path, including direction, timing, etc., of the liquid to the region in question may aid in improving the product's ability to contain bodily discharges.

In general, one reason why an absorbent article may be unable to adequately handle multiple discharges of liquid is the article's limitations regarding transporting discharged liquid away from the region of discharge, once the absorbent capacity of that region has been reached. Thus, the overall performance of the absorbent article may be affected by the article's properties with respect to transporting liquids to the various regions of the absorbent core, including regions that may be located away from the area where the discharged liquids first contact the absorbent core. Other performance characteristics relating to the interior of an absorbent article also may be of interest to a manufacturer. For example, information regarding how quickly various absorbent core materials absorb liquids, and how they then transport those liquids, may be helpful in product design and other contexts. In addition, information regarding actual fit—such as how the interior of the article actually contacts and contours the various body configurations—may be helpful in product design, manufacturing, marketing, and other contexts. Indeed, product fit may be of increased importance to various types of products, including various types of absorbent articles, when compared to others.

Methods for observing the interior of a consumer product and its packaging, and, more specifically, for observing the interior of a consumer product and its packaging, either as manufactured or as used, are provided. Disclosed are methods of observing product designs using techniques for obtaining data, such as imaging or scanning techniques. Any suitable imaging or scanning technique may be used with the present invention. Examples of suitable imaging processes include but are not limited to MRI, X-ray, computed tomography (CT) scan (e.g., two-dimensional CT and/or three-dimensional CT). Preferred examples include the use of MRI to image objects that are responsive to magnetic stimuli (e.g., generates an electromagnetic signal) and the use of CT to image objects independent of their responsiveness to magnetic stimuli. Generally, MRI images are generated by detecting the response of an object to a directed magnetic field. Accordingly, objects with mobile protons such as, for example, polymers with plasticizers, magnetically responsive agent (e.g., paramagnetic liquids, paramagnetic gels, real and/or synthetic body exudates), and the like may be imaged with a MRI system. Dry absorbent articles may not be visible with MRI, absent the introduction of the magnetically responsive agent into and/or upon a component of the absorbent article, i.e., the magnetically responsive agent may be imaged to provide information about the absorbent article. Since, CT imaging is not dependent upon magnetic stimuli, dry and/or wet absorbent articles may be imaged with or without a magnetically responsive agent, as described herein.

The methods described herein provide a means for evaluating performance characteristics of whole intact articles and/or articles in an in-use situation. Specifically, performance characteristics may be measured from an absorbent article, predicted with a virtual model using measured performance characteristics as input, and/or validated by data measured from an absorbent article.

As used herein, "absorbent article" refers to devices that absorb and contain body exudates, and, more specifically, refers to devices that can be placed against or in proximity to the body of a person to absorb and/or contain the various exudates discharged from the body. As used herein, the term "body fluids" or "body exudates" includes, but is not limited to, urine, blood, vaginal discharges, breast milk, sweat and fecal matter. Absorbent articles may include diapers, training pants, adult incontinence undergarments, feminine hygiene products, such as pads or tampons, breast pads, care mats, bibs, wound dressing products, and the like.

As used herein, "interior" refers to any portion of a product or packaging that is not readily visible to the naked eye viewing the exterior of the product or packaging. In some examples, the interior of a product or packaging may include one or more of internal surfaces and internal components of the product or packaging. In some examples, the interior may either include or exclude liquids, semi-solids, solids, emulsions, and colloids introduced into the product or packaging that may or may not interact with the product or packaging, but do not form an integral part of the product or packaging. Non-limiting examples would be urine or feces (actual or synthetic) introduced into a diaper.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be pre-formed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

As used herein, "voxel" refers to a basic unit of a three dimensional computed tomography image that is analogous to a pixel in a two-dimensional image and often displayed as a pixel in a computed tomography image display. Furthermore, it is noted that any portion of the present disclosure describing voxels in three-dimensions may also be extended to pixels in two-dimensions.

As used herein, "processor" refers to a computing device capable of executing machine readable instructions such as an integrated circuit, a microchip, a computer, and the like. It is noted that the examples described herein may comprise distributed computing devices. Specifically, multiple autonomous processors may be communicably coupled and configured to cooperate in a manner analogous to the single processor.

As is noted above, performance characteristics may be predicted (i.e., derived from a virtual model) or measured and/or derived from actual physical testing. Performance characteristics include any measurable parameter related to the overall performance of the absorbent article such as fluid handling, e.g. absorbency, fluid path, swelling of absorbent material, leakage, distribution of fluid, fluid management (e.g., retention, storage, capacity, acquisition), characteristics of how fluid goes into an absorbent structure, interaction of materials with an absorbent core, wicking, kinetics of fluid movement (e.g., acquisition rate). Performance characteristics also include fit of the article to a wearer. For example, performance characteristics pertaining to fit may include elastic components and their fit to the body, the behavior of absorbent material when dry/wet, fit of the product chassis on a body structure, e.g. mannequin, anatomical integration of the product with the body structure, article behavior during movement, etc.

Generally, a CT scan produces images of an object by collecting raw data indicative of X-ray projections (i.e., photons) that have been transmitted through the object and have been reconstructed into an image of the object. The object may be positioned between an X-ray detector and an X-ray source such that X-ray projections emitted by the X-ray source impinge upon the object and the X-ray detector. The final data set may be made more dimensionally complex than the X-ray detector by reconstructing a plurality of raw data sets collected by the X-ray detector. Specifically, the X-ray source may be configured to emit a collimated projection that is substantially linear. The projection line may travel through the object, wherein a portion of the projection is absorbed by the object, to a linear X-ray detector. The linear detector may then convert the detected linear projection into a raw data set. Alternatively, the X-ray source may be configured to emit a collimated projection that is substantially cone shaped. The cone shaped projection may travel through the object, wherein a portion of the projection is absorbed by the object, to a planar X-ray detector. The planar detector may then convert the detected planar projection into a raw data set.

Multiple raw data sets may be collected by causing relative motion of the object with respect to the X-ray source and/or X-ray detector. In one example, multiple raw data sets may be collected from the linear or planar detector by changing the position of the object with respect to the X-ray source and/or X-ray detector. For example, the object may be placed on a rotary table and rotated. As the object is rotated, multiple raw data sets can be collected as the X-ray source and X-ray detector remain fixed. Specifically, the object may be rotated about 360° with raw data sets produced by the X-ray source and X-ray detector at equal angular increments (e.g., 1440 raw data sets may by collected, with a raw data set collected after the object is rotated about 0.25°). Furthermore, the raw data sets may be collected by, for example, rotating an X-ray source and an X-ray detector with respect to the object, rotating an X-ray source with respect to the object and a plurality of X-ray detectors and/or rotating an X-ray detector with respect to the object and a plurality of X-ray sources.

The raw data sets may be reconstructed into an image of greater dimensional complexity than the X-ray detector (i.e., the raw data indicative of absorption or density of the object may be reconstructed into an object image indicative of both the internal and external features of the object). Specifically, raw data collected by a line detector may be utilized to produce a two-dimensional image showing a slice of the object that depicts both internal and external features. A plurality of slices may be combined to produce a full representation of the internal and external features of a three-dimensional object such as, for example, by combining slices collected along a direction orthogonal to the plane of the slices. Raw data collected by a planar detector may be utilized to produce a three-dimensional image of the three-dimensional object. Accordingly, a CT scan can detect and image internal and external features of an object without altering the object. It is to be understood that, while particular variations and principles may be discussed herein with regard to three-dimensional CT or other scanning techniques, any suitable imaging or scanning technique may be used with the present disclosure. It should further be understood that, unless otherwise stated, reference to imaging or to an imaging machine includes imaging machines, MRI, X-ray, CT, and any other applicable scanning or imaging technique or machine.

For illustrative purposes only, the methods described herein can include but are not limited to reconstructing raw data collected from a fixed planar X-ray detector and a fixed X-ray source with a rotating object into a three-dimensional CT data set. An exemplary X-ray CT measurement system is the FlashCT by Hytec Inc. of Los Alamos, N. Mex. Data may be collected with the FlashCT system set on mode 0 resolution (i.e., low resolution) or mode 1 resolution (i.e., high resolution) and an object set from about 1 mm to about 880 mm from the X-ray source with the detector from about 100 mm to about 880 mm from the X-ray source. The X-ray detector may have a resolution of about 1024×768 pixels at low resolution (pixels of about 388 µm) or about 2048×1536 pixels at high resolution (pixels of about 194 µm). The peak X-ray energy may be set from about 65 KVp (kilovolts, peak) to about 100 KVp (kilovolts, peak) with a current from about 250 µA to about 100 µA. The integration time may be from about 33 msec to about 1 sec.

Specifically, when a relatively low amount of penetration is desired, data may be collected with the FlashCT system set on mode 1 resolution and an object set at 700 mm from the X-ray source with the detector 880 mm from the X-ray source. The X-ray detector may have a resolution of about 2048×1536 pixels (pixels of about 194 mm). The peak X-ray energy may be set to about 65 KVp (kilovolts, peak) with a current of about 250 µA with an integration time of about 267 msec. Alternatively, when a relatively high amount of penetration is desired, data may be collected with the FlashCT system set on mode 1 resolution and an object set at 700 mm from the X-ray source with the detector 880 mm from the X-ray source. The X-ray detector may have a resolution of about 2048×1536 pixels (pixels of about 194 µm). The peak X-ray energy may be set to about 80 KVp (kilovolts, peak) with a current of about 200 µA with an integration time of about 267 msec. The FlashCT system may generate raw data with a resolution of about 2048×2048 pixels (pixels of about 154 µm) at capture. About 3200 raw data sets (i.e., projections) from the two-dimensional X-ray detector may be reconstructed into three-dimensional CT data set depicting internal and external features of the scanned object.

In the present disclosure, any of the consumer products, portions or constituents thereof, packaging, etc. identified above may be evaluated by imaging techniques to obtain any information of interest, including but not limited to information relating to fluid distribution and containment, fluid flow and transport, product fit, product performance, packaging integrity, product density distribution, how a product fills its packaging, etc. In one example, a model (such as a mannequin) adapted to display (or wear) an absorbent article can be placed in an imaging machine for testing purposes (e.g., mounted to a rotating table of a CT system). In another example, the model may be a mannequin adapted to accommodate fluids or semi-solids that come in contact with the product. In other examples, a portion of a product, or constituents of a product, may be placed in an imaging machine. In other examples, product packaging may be placed into an imaging machine. In other examples, a product or a portion or constituent thereof that is inside packaging may be placed inside an imaging machine.

In some examples of the present invention, where applicable, the product may be placed on a model so as to obtain information relating to how the product performs or responds under actual product usage conditions. The model may be one that represents, that simulates, etc. conditions for actual product usage. The model may have various features that enable the product to be used in a manner that simulates actual usage with respect to the information of interest. For example, where the product of interest is an absorbent article, such as a diaper, the model may take the form of a frame over which the diaper is positioned, or the model may take the form of a mannequin that represents the applicable anatomical geometry of the product's user. Where a mannequin is used, features that simulate actual product usage may include a tube and artificial orifice, or more than one of each, to enable transport of fluid, solid, or semi-solid materials from the inside of the mannequin to the absorbent article from an anatomically correct location, such as in a manner that represents soiling of a diaper by urine from a urethra, fecal matter from a rectum, or both. Specifically, the tube may be dimensioned, constructed, sized, and positioned to simulate a urethra and/or a rectum.

The mannequin may be indicative of an actual person and/or a group of people (i.e., a composite of features from a group or a statistical representation of a group of people). Specifically, as described by U.S. Patent Application No. 2008/0015537 assigned to The Procter & Gamble Company of Cincinnati, Ohio, the pertinent portions of which are incorporated by reference herein, a mannequin may be constructed to correspond to a suitable model infant (e.g., an infant weighing approximately 11.8 kilograms and had proportions typical for a median child in the recommended weight range for PAMPERS size 4 Easy Ups (7.3-15.4 kilograms)). A photographic surface scan of the infant may be taken using a 3 dMD 5 pod torso photographic system (available from 3 dMD of Atlanta, Ga.). The surface data from the scan may be enhanced electronically in areas with poor polygon coverage (e.g. perineum creases). A mannequin master may be created using stereolithographic equipment as a hard polymer shell. A molded mannequin may be generated from the shell. A suitable mannequin is disclosed in commonly assigned, co-pending U.S. Ser. No. 13/161,722, entitled "Mannequins for Use in Imaging and Systems Including the Same", filed on 16 June, 2011.

It should be understood that the mannequin can be of varying sizes to simulate varying human sizes such as, for example, an adult, a child or an infant human, as well as male or female. This permits evaluation of different products for different users. The mannequin can be of any desired configuration and geometry to represent any given body size, shape, or composition. The mannequin may have a hollow interior portion, which may be adapted to receive a dispenser. Alternatively, the mannequin may comprise a foam disposed in the interior portion. The dispenser can carry either fluid and/or semi-solids to the mannequin. Alternatively, the dispenser or multiple dispensers, may be disposed within the mannequin. The mannequin may comprise more than one dispenser such that both urine and fecal incidents can be simulated. The fluids or semi-solids can exit the dispenser and mannequin through an opening in the mannequin. The product may be oriented such that it is adjacent the opening of the mannequin and may be adapted to receive the exited contents of the dispenser. The liquids and/or semi-solids can be moved through the mannequin in any desired manner. For example, the rate, quantity, consistency, frequency, etc. of fluid and/or semi-solid flow can be varied to represent any combination of parameters of interest. Doing so can provide information, for example, as to how well the article contains and distributes fluids when worn by a 10 pound boy child who sleeps on his side, or how well an article contains runny fecal material when worn by an incontinent two-hundred and twenty pound adult female, etc.

Figure 1:
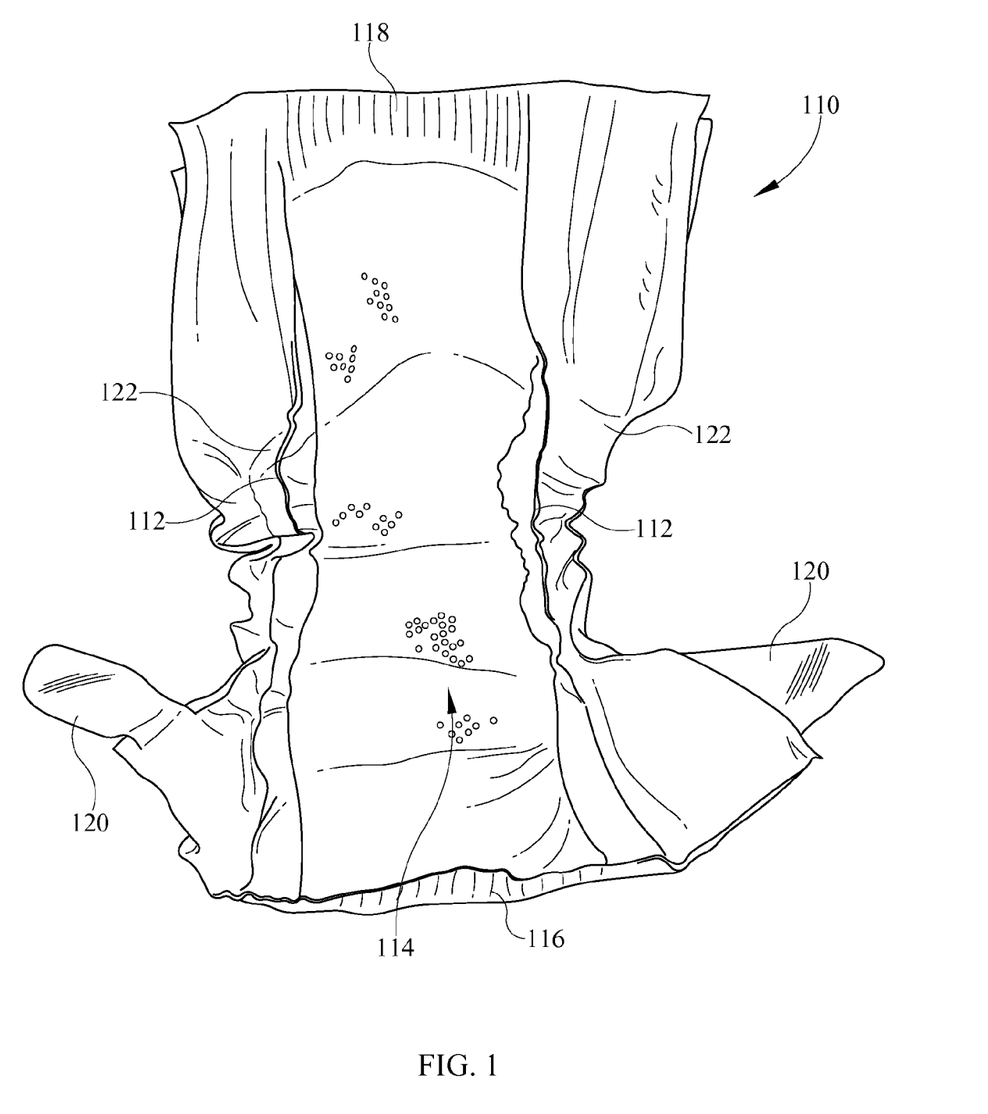
FIG. 1 schematically depicts an absorbent article according to one or more examples shown and described herein.

FIG. 1 depicts an absorbent article 110 in accordance with one example of the present disclosure. The absorbent article 110 may comprise sealing members 112 and an absorbent core 114. The sealing members 112 may be any type of flexible gasket configured to mitigate the flow of fluid between a wearer of the absorbent article 110 and the sealing members 112 such as, for example, a barrier leg cuff. The absorbent core 114 may comprise any flexible material capable absorbing and retaining a fluid (e.g., an assembly including a topsheet, an absorbent interior, and a backsheet).

Figure 2:
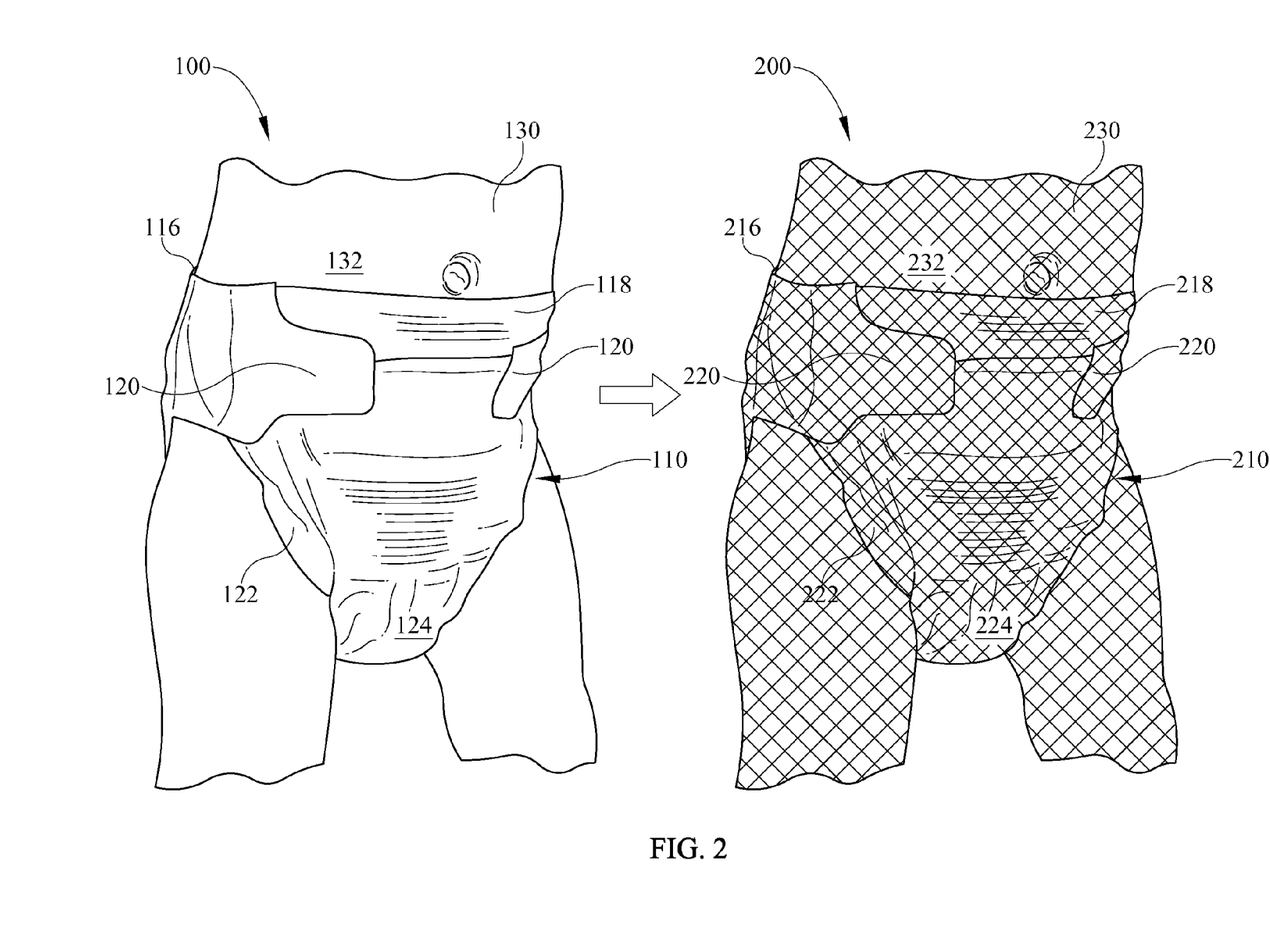
FIG. 2 schematically depicts a transformation of a physical system to a three-dimensional computed tomography data set according to one or more examples shown and described herein.

The absorbent article 110 may further comprise a first half waistband 116, a second half waistband 118, anchoring members 120 and leg cuffs 122. The first half waistband 116 and the second half waistband 118 may be elastically deformable and configured to fit around a waist of a wearer and/or an analog device when the first half waistband 116 and the second half waistband 118 are anchored to one another. The sealing members 112, the absorbent core 114, and the leg cuffs 122 may extend from the first half waistband 116 to the second half waistband 118. The anchoring members 120 may be permanently attached to the first half waistband 116 and configured for attachment to the second half waistband 118. Referring collectively to FIGS. 1 and 2, the absorbent article 110 may further comprise an outer cover 124 that is laterally stretchable and coupled to the sealing members 112 (FIG. 1), the absorbent core 114 (FIG. 1), the leg cuffs 122, the first half waistband 116, and the second half waistband 118.

Referring to FIG. 2, a physical system 100 may comprise an absorbent article 110 mounted to a mannequin 130. As is depicted in FIG. 2, the mannequin 130 may simulate a baby or child wearing an absorbent article 110 in a standing position. To obtain information regarding absorbent article 110 in this context, the absorbent article 110 can be placed on the mannequin 130 in a manner that represents how the article is commonly worn. The physical system 100 can be configured to predict, measure and/or derive the performance characteristics of the absorbent article 110. Specifically, the physical system 100 may be transformed into image space for analysis. In one example, the physical system 100 may be scanned and reconstructed into a three-dimensional computed tomography data set 200 indicative of the physical system 100, as is described hereinabove. The three-dimensional computed tomography data set 200 may comprise an article image 210 and a mannequin image 230. The article image 210 may be indicative of the absorbent article 110. The mannequin image 230 may be indicative of the mannequin 130. For example, the article image 210 may be constructed from projections collected while the absorbent article 110 is fitted to the mannequin 130. Accordingly, the article image 210 may comprise sealing member images 212 (FIG. 4), an absorbent core image 214 (FIG. 3), leg cuff images 222, a first half waistband image 216, a second half waistband image 218, and an outer cover image 224 in image space. While the mannequin 130 is depicted in FIG. 2 in a standing position, it is noted that mannequins suitable for use with the examples described herein may model a wearer in a prone position, a sitting position, or any other position likely to provide information indicative of performance characteristics of an absorbent article.

Figure 3:
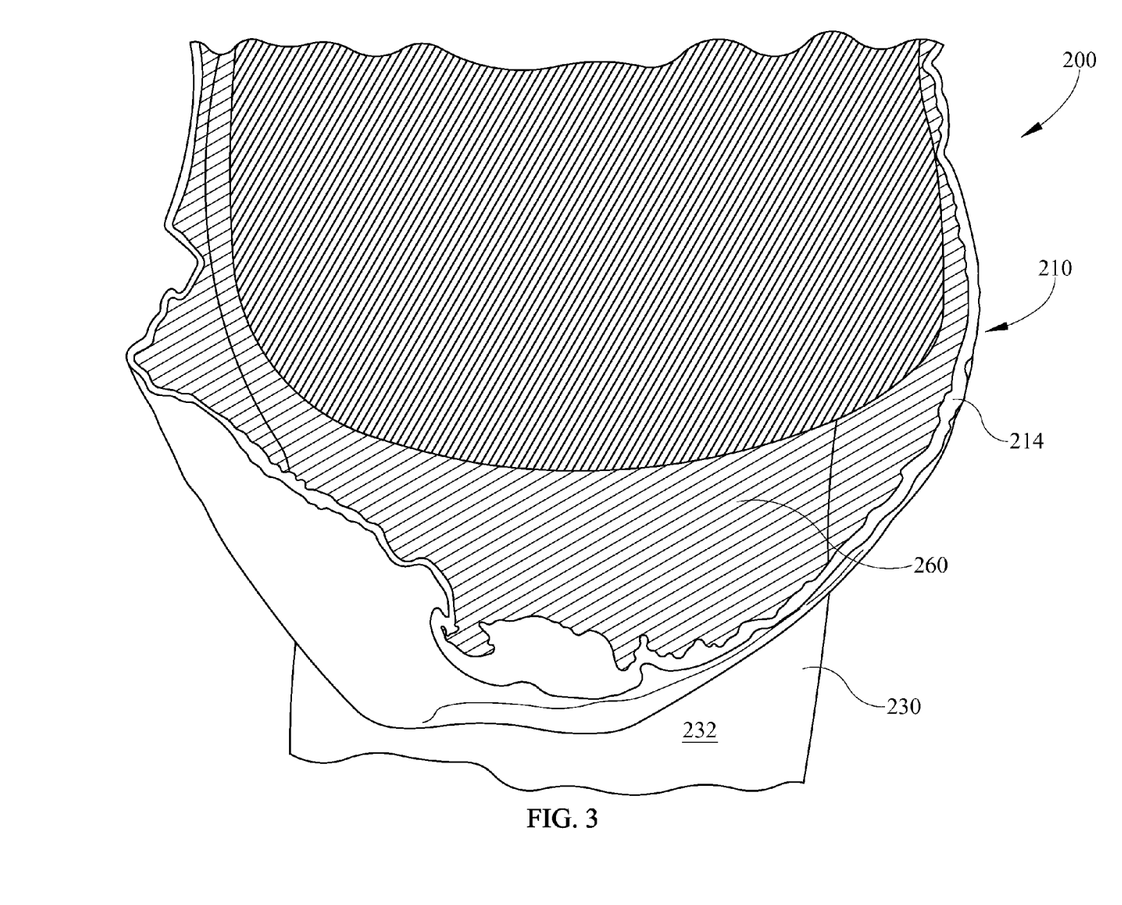
FIG. 3 schematically depicts a three-dimensional computed tomography data set according to one or more examples shown and described herein.

As is noted above, the three-dimensional computed tomography data set 200 may be reconstructed into an image indicative of both the internal and external features of the physical system 100. Thus, as depicted in FIG. 3, any portion of the three-dimensional computed tomography data set 200 may be displayed by visualization software such as, for example, Avizo by Visualization Sciences Group of Burlington, Mass. It is noted that internal features of the three-dimensional computed tomography data set 200 may be observed in order to predict, measure and/or derive performance characteristics such as, for example, a contact pressure of a sealing member 112 (FIG. 1) of the absorbent article 110, a tension of the sealing member 112 of the absorbent article 110, a height of the sealing member 112 of the absorbent article 110, a length of the sealing member 112 of the absorbent article 110, a thickness of the absorbent article 110, a stiffness of the absorbent article 110, fit measurements, e.g. the dimensions, e.g. length and/or width, of the gap(s), if any between any portion of the absorbent article 110, e.g. a sealing member 112, and a mannequin 130, and/or a compression of the absorbent article 110.

In addition to internal features, external features of the three-dimensional computed tomography data set 200 may be evaluated. Specifically, image processing algorithms may be applied to the three-dimensional computed tomography data set 200 to transform the entire data set and/or a portion thereof. The image processing algorithms may be executed automatically with a processor such as, for example, as a function of the visualization software to analyze internal and external features. Image processing algorithms may include: color corrections (e.g., contrast, opacity, grayscale, color mapping), image filters (e.g., minimum filter, maximum filter, unsharp masking, Laplacian edge detector filter (i.e., Laplacian zero-crossing), median filter, Gaussian smoothing filter, Sobel edge detection filter, equalize filter (i.e., contrast limited adaptive histogram equalization), edge preserving filter, resampling/low pass filter (i.e., Lanczos), intensity remapping filter (i.e., Sigmoid), brightness/contrast filter, statistical feature detection filter (i.e., centralized moment calculations), lighten/darken filter (i.e., gamma correction)), connected components, image cropping, image segmentation, image registration, morphological dilation, morphological erosion, thresholding, windowing, mapping operations (i.e., curves, surfaces or regions), and animation (i.e., time based, along a camera path or selected regions).

Figure 4:
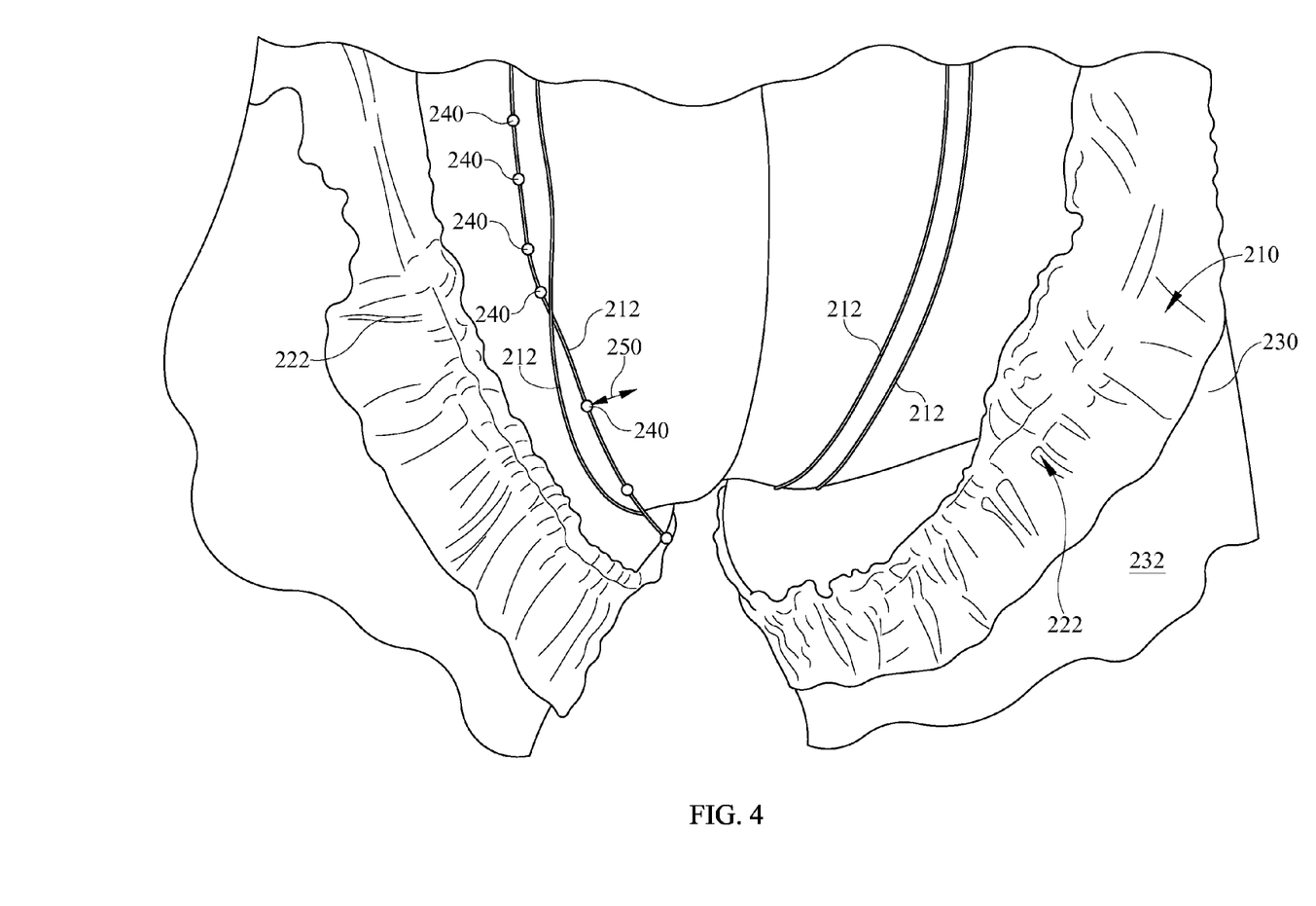
FIG. 4 schematically depicts a three-dimensional computed tomography data set according to one or more examples shown and described herein.

Referring collectively to FIGS. 2 and 4, an outer surface 232 of the mannequin image 230 may be identified such as, for example, by using visualization software. Portions of the three-dimensional computed tomography data set 200 unrelated to the mannequin image 230 may be cropped (i.e, removed from the image or no longer displayed) from the three-dimensional computed tomography data set 200. After the three-dimensional computed tomography data set 200 is cropped, a median filter may be applied to the three-dimensional computed tomography data set 200 for data smoothing. Then the three-dimensional computed tomography data set 200 may be thresholded to remove voxels from the three-dimensional computed tomography data set 200 that have values that do not correspond to the value of voxels on the outer surface 232 of the mannequin image 230. For example, a voxel on the outer surface 232 of the mannequin image 230 may be selected and used to set a range of acceptable values that correspond to voxels likely located on the outer surface 232. Thus, the range of acceptable values can vary depending on the values and scale of the voxels (i.e., the voxels may be down sampled to any size such as about 130 µm, about 250 µm or about 520 µm) in the three-dimensional computed tomography data set 200. The thresholded data set may be over-inclusive (i.e., include voxels not located on the outer surface 232) and/or under-inclusive (i.e., omit voxels located on the outer surface 232).

In such cases, a connected components algorithm may be applied to a voxel known to be on the outer surface 232. The connected components algorithm may be utilized to connect voxels on the outer surface 232 and thus, identify the outer surface 232. The connected component algorithm may identify voxels within a voxel value range (e.g., gray scale value or intensity) that are connected to a starting voxel (i.e., a chain of voxels having values within the range that are linked by a common face, common edge and/or a common vertex.) Once the appropriate voxels corresponding to the outer surface 232 have been identified, the outer surface 232 may be utilized for analysis. In one example, binary values indicative of whether or not a given three-dimensional coordinate may be generated and multiplied by three-dimensional computed tomography data set 200 to extract the outer surface 232 from the three-dimensional computed tomography data set 200. In further examples, the outer surface 232 may be automatically identified. For example, the three-dimensional computed tomography data set 200 may be registered to a known coordinate system wherein the outer surface 232 of the mannequin image 230 is predefined, i.e., the three-dimensional computed tomography data set 200 may be aligned with a corresponding three-dimensional data with a pre-defined mannequin outer surface.

Referring to FIG. 4, a relevant portion of the article image 210 may be enhanced. As an example, a desired distance may be defined when an internal or external feature of the article image 210 is known to be within the desired distance away from the outer surface 232 of the mannequin image 230. A volumetric demarcation may be spaced the desired distance away from the outer surface 232 of the mannequin image 230. Specifically, the volumetric demarcation may be defined by transforming the outer surface 232 and the desired distance with a Euclidean distance map, i.e., the volumetric demarcation may be defined as a contour that is offset the desired distance away from the outer surface 232. An image volume may be disposed between the outer surface 232 of the mannequin image 230 and the volumetric demarcation. In another example, a morphological dilation may be applied to the outer surface 232 to define the image volume. For example, each of the voxels disposed on the outer surface 232 may be dilated by several voxels to define the volumetric demarcation such that the image volume is within the dilated region. If the outer surface 232 is dilated by 10 voxels, the image volume would include the portion of the three-dimensional computed tomography data set 200 within 10 voxels of the outer surface.

The relevant portion of the article image 210 may be enhanced by obscuring an undesired portion of the three-dimensional computed tomography data set 200. Specifically, the relevant portion of the article image 210 may be coincident with the image volume and undesired portion of the three-dimensional computed tomography data set 200 may not be coincident with the image volume. Thus, the relevant portion may be enhanced by transforming the three-dimensional computed tomography data set 200 with an image processing algorithm. For example, differing image processing algorithms may be applied to the undesired portion and the relevant portion. Specifically, different types of filter operations may be applied to the undesired portion and the relevant portion. In one example, color corrections may be applied to the undesired portion and the relevant portion to improve the visibility of the relevant portion. In another example, the image volume may be used to mask away the undesired portion of the three-dimensional computed tomography data set 200 (i.e., removing the undesired portion from three-dimensional computed tomography data set 200 and/or not displaying the undesired portion). Thus for example, the masked dataset may be used to analyze features and/or components of the article image 210 that are within the desired distance of the outer surface 232 (e.g., cuff elastics of a diaper).

Referring to FIGS. 1 and 4, the absorbent article 110 may comprise sealing members 112 and leg cuffs 122. The relevant portion of the article image 210 may be selected such that the relevant portion comprises sealing member images 212 that are indicative of the sealing members 112 (e.g., a pair of barrier leg cuffs of a diaper, each comprising, e.g. one or more elastic members therein). Specifically, the desired distance may be set to less than about 10 mm on a masked image such as, for example, greater than 0 mm and less than about 10 mm, greater than 0 mm and less than or equal to about 5 mm, or greater than 0 mm and less than or equal to about 1 mm. The relevant portion of the article image 210 may also comprise leg cuff images 222 that are indicative of the leg cuffs 122. As is depicted in FIG. 4, the sealing member images 212 may be evaluated after the relevant portion has been enhanced by a masking operation. Moreover, the leg cuff images 222 and/or the sealing member images may be enhanced by setting the desired distance to less than about 10 mm on a masked image such as, for example, greater than 0 mm and less than about 10 mm, greater than 0 mm and less than or equal to about 5 mm, or greater than 0 mm and less than or equal to about 1 mm.

Referring now to FIG. 4, multiple spatial locations 240 of the article image 210 may be identified. As an example, the spatial locations 240 may be selected with a voxel selection tool of the visualization software such that the spatial locations 240 are along one of the sealing member images 212 (e.g., along a portion of the image corresponding to a barrier leg cuff). The spatial locations 240 may be utilized to directly calculate a shortest distance 250 between the sealing member image 212 that corresponds to the spatial locations 240 and the outer surface 232 of the mannequin image 230.

The spatial locations 240 may also be utilized to indirectly calculate a shortest distance 250 between the sealing member image 212 and the outer surface 232 of the mannequin image 230. For example, the multiple spatial locations 240 may be selected along an object in the relevant portion of the article image 210 such as, for example, a sealing member image 212. A B-spline defining algorithm may fit a B-spline to the spatial locations 240 (e.g., from about 10 points to about 20 points) and thus, define a spline that is disposed within the relevant portion of the article image 210. Specifically, the spatial locations may be used as control points to define a B-spline having a desired degree. As the degree is increased, the number of control points may need to be increased, the resultant B-spline may be smoother, and the number of oscillations may increase. It is noted that, while B-splines are described above, any smoothing or interpolating curve fitting algorithm may be utilized.

Figure 5:
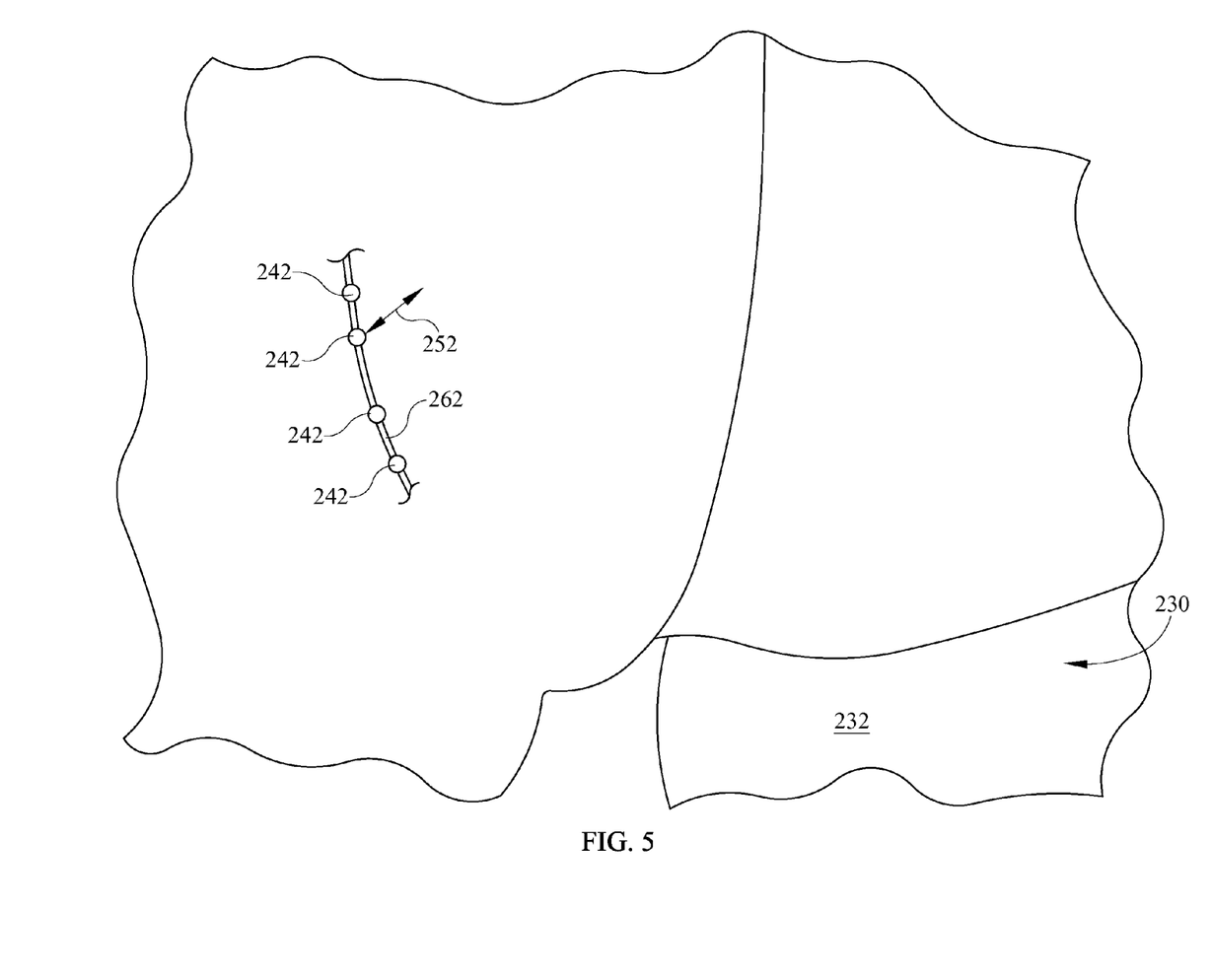
FIG. 5 schematically depicts a three-dimensional computed tomography data set according to one or more examples shown and described herein.

Referring now to FIG. 5, a three-dimensional spline 262, defined as described above, can be used to create a path through the relevant portion of the article image 210. The three-dimensional spline 262 may comprise a plurality of spline points 242 disposed along the three-dimensional spline 262. Any number of spline points 242 may be generated along the three-dimensional spline 262 and used to characterize the article image 210. For example, the spline points 242 may be placed at equal intervals along the three-dimensional spline 262. Alternatively, portions of the three-dimensional spline 262 corresponding to particular regions of interest may have more or less spacing between spline points 242, depending on the desired analysis. In one example, three-dimensional spline 262 and the spline points 242 correspond to a barrier leg cuff of a diaper. The distance between the barrier leg cuff and the mannequin 130 may be approximated by automatically calculating the shortest distance 252 (e.g., Euclidean distance) between each of the spline points 242 and the outer surface 232 of the mannequin image 230. Once all of the distances are calculated, the distances may be plotted on the outer surface 232 a visual test of the validity of the calculation. Alternatively, the distances can be output to a spreadsheet and/or input into a virtual model. Accordingly, a performance characteristic may be generated by the virtual model data from the relevant portion of the article image 210. Optionally, the performance characteristic can be based substantially upon data measured from the relevant portion of the article image 210, i.e., the performance characteristic may be calculated directly from the measured data.

Referring again to FIGS. 1, 2 and 3, portions of article image 210 and/or the mannequin image 230 may be "cut" away to reveal features (internal and external) not visible in the physical system 100. Specifically, a capture volume may be disposed between the mannequin 130 and the absorbent article 110. The capture volume may not be visible in the physical system 100. Moreover, portions of the absorbent article 110 and interactions between the absorbent article 110 and the mannequin 130 may not be visible in the physical system (e.g., deformation of the mannequin caused by the absorbent article 110). Since any suitable filtering technique can be used to filter out products, mannequins, packages, and other areas that are not of interest in a given test or application, various in-use conditions may be simulated by the physical system 100 while the projections are collected.

For example, a capture volume image 260 that is indicative of a capture volume bounded by the mannequin 130 and the absorbent article 110 may be made visible by the visualization software. Therefore, when projections are collected from a wet or dry article, the capture volume image 260 may be evaluated to determine dry and/or wet performance characteristics. Specifically, the volumetric dimensions of the capture volume image 260 may be quantified with a connected component analysis, as is described above. Moreover, the internal dimensions of any portion of the article image 210 may be revealed. For example, the internal features of the absorbent core image 214 may be evaluated under wet and/or dry conditions. The size, location, and intensity of the absorbent core image 214, which may swell when wetted, can be measured and used for virtual modeling purposes. Isolating the absorbent core image 214 may provide performance characteristics regarding how the absorbent core 114 will perform in-use conditions, how the geometry of the absorbent core 114 changes, and how those geometry changes affect fit and how they affect the ability of the absorbent core 114 to absorb and distribute subsequent liquid discharges, how the absorbent core 114 affects adjacent and surrounding article components as it absorbs fluid and changes geometry, etc.

In some situations it may be desirable to simulate in use conditions of the absorbent article 110 by collecting projections from an absorbent article 110 throughout various states of dryness, wetness, or both. Performance characteristics correlated with a dry absorbent article may be simulated by collecting projections while the absorbent article 110 is dry. Performance characteristics correlated with a wet absorbent article may be simulated by collecting projections while at least a portion of the absorbent article 110 is wet. Performance characteristics correlated with a wet absorbent article may also be simulated by collecting projections while a substantial portion of the absorbent article 110 is wet (e.g., the absorbent article 110 may be subjected to multiple or repeated introductions of fluid, solid, or semi-solid materials).

Projections may be collected over any suitable period of time. The period of time that is suitable will vary based on the product, the context in which it is being evaluated, energy level of the X-ray source and the frame rate of the X-ray sensor. For example, with an absorbent article 110, such as a diaper, in some examples, projections may be collected by the X-ray sensor at a frame rate of about 3.75 frames per seconds. Optionally, when four frames are collected per projection (averaged to increase signal to noise ratio), about 3200 projections may be collected which require about 1 hour of data collection. The amount of time required to collect projections may be decreased by reducing the number of frames that are averaged, reducing the number of projections collected, and/or increasing the power level of the X-ray source. However, image quality may be reduced, i.e., increase noise, increased image artifacts and reduced image resolution.

Once collected, the projections can be reconstructed and used in any suitable fashion. For example, different camera angles of an entire three-dimensional CT data set, or any portion thereof may be played in succession, like a movie. Moreover, projections may be collected more rapidly (i.e., increased power level and/or reduced number of projections per reconstruction) as fluid, a solid and/or a semi-solid is introduced by the mannequin 130 and may be reconstructed into a plurality of three-dimensional CT data sets. The plurality of three-dimensional CT data sets may be played in succession to allow a viewer to observe the intensity, location, path, etc. of the fluid, the solid and/or the semi-solid.

Referring again to FIG. 2, a first three-dimensional computed tomography data set comprising a first article image and a second three-dimensional computed tomography data set comprising a second article image may be reconstructed as described herein. The first three-dimensional computed tomography data set and the second three-dimensional computed tomography data set may be constructed from projections collected while an absorbent article 110 is fitted to a mannequin 130. The projections may be collected over sequential time periods. That is, the first article image may be indicative of the absorbent article 110 throughout a first time period, and the second article image may be indicative of the absorbent article 110 throughout a second time period. The first time period and the second time period may overlap or encompass non-overlapping durations of time. When the first time period and the second time period are sequential, the flow of material introduced by the mannequin may be tracked. For example, the absorbent article 110 may be observed with and/or without material such as, for example, fluid, a solid and/or a semi-solid.

Figure 6:
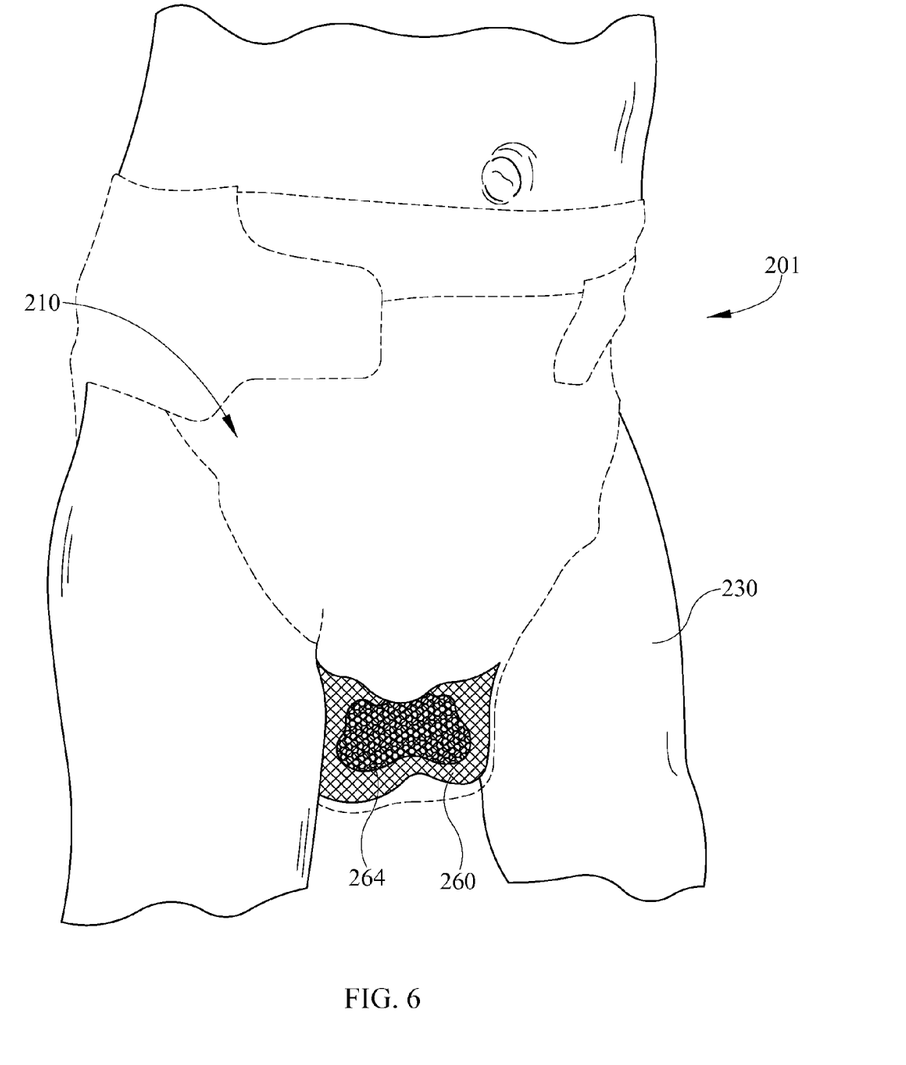
FIG. 6 schematically depicts a three-dimensional computed tomography data set according to one or more examples shown and described herein.

Referring to FIG. 6, the first three-dimensional computed tomography data set 201 may comprise a fluid image 264 indicative of a fluid throughout the first time period. The fluid image 264 of FIG. 6 is indicative of a quantity of fluid disposed in a capture volume. However, it is noted that fluid images may be collected such that the fluid is in any position of the first three-dimensional computed tomography data set 201 such as, for example, a quantity of fluid disposed between a sealing member and a mannequin and/or a quantity of fluid absorbed by an absorbent core, and/or any other position.

As discussed above, fluid images can be used to monitor fluid flow. This information can help identify materials that provide better performance characteristics in terms of liquid absorption and containment, leak prevention, liquid dispersion and wicking, elasticity, etc. This information also can be collected in various model positions. For example, in the case of a diaper, the information enables evaluation of liquid containment as the child is in various positions, as the diaper is fastened or secured in different ways, etc. In the case of liquid containment, the information can be used to identify the location or locations where liquid is escaping from the article, the positions of the child when this occurs, the ways the diaper is attached when this happens, the path that the fluid follows as it moves from the site of deposition to the site of leakage, etc.

CT data also is useful for evaluating product fit. For example, where the product is a diaper, fit can be evaluated before, during, and after single or multiple liquid depositions; as the child is in different positions; as the diaper is secured by a caretaker in different ways (tightness, position of tape on landing zone, location on hips, etc.), and subsets and combinations of the above.

Many materials commonly used for diapers, such as polyethylene and polypropylene, may not be visible using certain imaging techniques, such as MRI. Therefore, in order to visualize product fit, and in this example, diaper chaffing or other product attributes of interest, adjustments to the product may be made. For example, surgical tubing can be filled with a liquid that is visible to an MRI machine. Any suitable liquid may be used. For example, the surgical tubing may be filled with Magnevist doped saline.

It should now be understood that virtual models and CT data may be compared for validation. When testing and designing products, virtual models of the products may be used to estimate performance characteristics such as fit and/or location. In one example cuffs of a diaper can be transformed into an image by an imaging machine. For example, data is retrieved with respect to the location of the cuffs shown by the imaging machine and imported into a software package.

Where the product is an absorbent article such as a diaper, these methods also enable evaluation of fit as the product is worn, before, during, and/or after one or more depositions of a fluid, a solid or a semi-solid material into the article. The methods also enable evaluation of how fit is affected by wear of the article, user movement, deposition into the article of fluids, solids, and semi-solids, other conditions, and combinations of these. The information obtained may be used in any of a variety of ways. Where the product is an absorbent article, such as a diaper, the information enhances evaluation of the article's performance, in terms of absorbing fluids, distributing fluids, containing fluids, etc.

The information also may enhance product design. For example, the goal of an article, as for a young baby, may be to keep the child dry and comfortable. In contrast, where the article is intended for use with an older child who may be in the potty training stage, the purpose of the article may be to contain exudates and prevent leaks, while simultaneously maintaining some level of contact between the child and the exudates to prevent the child from being overly comfortable after soiling the article. The techniques of the present invention provide information, such as that based on visual observation, relating to how fluids and semi-solids contact the child as the diaper is worn, which may be useful to the product's designers.

Although the present disclosure makes reference to particular examples, persons skilled in the art will recognize that changes may be made in form and detail without departing from the spirit and scope of the disclosure. All directional references (e.g., rear, front, left, right, top, bottom) are only used for identification purposes to aid the reader's understanding of the examples of the present invention, and do not create limitations, particularly as to the position, orientation, or use of the invention unless specifically set forth in the claims. It is intended that all matter contained in the above description or shown in the accompanying drawings shall be interpreted as illustrative only and not as limiting. Changes in detail or structure may be made without departing from the spirit of the disclosure as defined in the appended claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference, however the citation of any document is not construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular examples have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for analyzing an absorbent article, the method comprising:
   providing a three-dimensional computed tomography data set comprising a mannequin image and an article image, wherein the article image is constructed from projections collected while the absorbent article is fitted to a mannequin;
   identifying an outer surface of the mannequin image;
   providing a desired distance, wherein a volumetric demarcation is spaced the desired distance away from the outer surface of the mannequin image and an image volume is disposed between the outer surface of the mannequin image and the volumetric demarcation; and
   enhancing, using a processor, a relevant portion of the article image, wherein the relevant portion of the article image is coincident with the image volume.

2. The method of claim 1 wherein the relevant portion of the article image is enhanced by transforming the three-dimensional computed tomography data set with an image processing algorithm.

3. The method of claim 2 wherein an undesired portion of the three-dimensional computed tomography data set is obscured from the three-dimensional computed tomography data set, and the undesired portion is not coincident with the relevant portion of the article image.

4. The method of claim 2 wherein the relevant portion of the article image is separated from the three-dimensional computed tomography data set.

5. The method of claim 1 wherein differing image processing algorithms are applied to an undesired portion of the three-dimensional computed tomography data set and the relevant portion of the article image.

6. The method of claim 1, further comprising:
   identifying multiple spatial locations of the article image; and
   calculating a shortest distance from each of the multiple spatial locations to the outer surface of the mannequin image.

7. The method of claim 6 wherein the multiple spatial locations define a three-dimensional spline and the three-dimensional spline is disposed within the relevant portion of the article image.

8. The method of claim 6 wherein the multiple spatial locations correspond to a barrier leg cuff.

9. The method of claim 1, further comprising evaluating a performance characteristic of the absorbent article, wherein the performance characteristic is based at least in part upon data measured from the relevant portion of the article image.

10. The method of claim 9 wherein the performance characteristic is a fluid handling parameter, an absorbency parameter, a fluid path parameter, a swelling parameter, a leakage parameter, a fluid distribution parameter, a fluid retention parameter, a fluid storage parameter, a fluid capacity parameter, a fluid acquisition parameter, a fluid kinetics parameter, a fit of the absorbent article to the mannequin, or combinations thereof.

11. The method of claim 10 wherein the performance characteristic is the absorbency parameter, the leakage parameter, the fluid acquisition parameter, the fit of the absorbent article to the mannequin, or combinations thereof.

12. The method of claim 11 wherein the performance characteristic is the fit of the absorbent article to the mannequin.

13. The method of claim 1, further comprising predicting a performance characteristic of the absorbent article with a virtual model, wherein the performance characteristic is based at least in part upon data measured from the relevant portion of the article image.

14. The method of claim 13, wherein the performance characteristic is based substantially upon the data measured from the relevant portion of the article image.

15. The method of claim 1, further comprising validating a performance characteristic of the absorbent article with data measured from the relevant portion of the article image.

16. The method of claim 15 wherein the performance characteristic is a fit of the absorbent article to the mannequin.

17. The method of claim 1 wherein the projections are collected while the mannequin is deformed by the absorbent article.

18. The method of claim 1 wherein the projections are collected while the absorbent article is dry.

19. The method of claim 1 wherein the projections are collected while at least a portion of the absorbent article is wet.

20. The method of claim 19 wherein the projections are collected while a substantial portion of the absorbent article is wet.

21. The method of claim 1 wherein the projections are collected while the absorbent article is in contact with a magnetically responsive agent.

22. The method of claim 1 wherein the projections are collected while the absorbent article is not in contact with a magnetically responsive agent.

23. The method of claim 1 wherein the desired distance is less than about 10 mm.

24. The method of claim 23 wherein the desired distance is greater than 0 mm and less than or equal to about 5 mm.

25. The method of claim 24 wherein the desired distance is greater than 0 mm and less than or equal to about 1 mm.

* * * * *